United States Patent [19]

Sotirianos

[11] 4,148,590
[45] Apr. 10, 1979

[54] APPARATUS AND METHOD OF STIRRING FLUIDS

[75] Inventor: Konstantin Sotirianos, Stäfa, Switzerland

[73] Assignee: Dr. Ing. Hans Müller, Maennedorf, Switzerland

[21] Appl. No.: 853,575

[22] Filed: Nov. 21, 1977

Related U.S. Application Data

[63] Continuation of Ser. No. 723,883, Sep. 16, 1976, abandoned.

[30] Foreign Application Priority Data

Sep. 25, 1975 [CH] Switzerland .................. 12488/75

[51] Int. Cl.² ............................................. B01F 9/22
[52] U.S. Cl. .................................... 366/288; 366/280
[58] Field of Search ............... 366/287, 288, 280, 317, 366/279, 297, 300

[56] References Cited

U.S. PATENT DOCUMENTS

| | | | |
|---|---|---|---|
| 2,170,280 | 8/1939 | Sharp | 259/102 |
| 2,571,366 | 10/1951 | Jennings | 259/108 |
| 3,299,896 | 1/1967 | Sabbaides | 366/280 |
| 3,785,621 | 1/1974 | Hoskins | 366/287 |

*Primary Examiner*—Robert W. Jenkins
*Attorney, Agent, or Firm*—Michael J. Striker

[57] ABSTRACT

A biological fermentor and improved method of aerating micro-organisms contained in the fermentor include a rotor which is mounted in the fermentor for turning movement in one direction, and a baffle element which is mounted on the rotor for turning movement with the same and also relative thereto in a different opposite direction. A motor is operative for turning the rotor and baffle element in their respective directions so as to strongly agitate the contents of the fermentor.

12 Claims, 8 Drawing Figures

I   ROTATING BAFFLE ELEMENTS
II  FIXED BAFFLE ELEMENTS

MIXER WITH ROTATING BAFFLE ELEMENTS

TEST RESULTS: (MEDIUM: WATER = 11 LITERS)

a) WITH 4 BAFFLE ELEMENTS

| RPM | AMPERES | WATTS | MIXING EFFECT |
|-----|---------|-------|---------------|
| 100 | 1.0 | 40 | GOOD |
| 200 | 1.4 | 60 | VERY GOOD (TURBULENCE) |
| 300 | 1.6 | 80 | STRONG |
| 400 | 2.0 | 100 | VERY STRONG |
| 500 | 2.8 | 150 | VERY STRONG TURBULENCE |
| 600 | 3.5 | 200 | " " " |
| 700 | 4.5 | 300 | " " " | b) WITH 2 BAFFLE ELEMENTS

| RPM | AMPERES | WATTS | MIXING EFFECT |
|-----|---------|-------|---------------|
| 100 | 0.7 | 20 | WEAK |
| 200 | 1.0 | 40 | GOOD |
| 300 | 1.5 | 50 | " |
| 400 | 2.3 | 90 | VERY GOOD (TURBULENCE) |
| 500 | 2.6 | 115 | " " " |
| 600 | 2.8 | 150 | STRONG TURBULENCE |
| 700 | 3.0 | 180 | VERY STRONG TURBULENCE |
| 800 | 3.4 | 205 | " " " |
| 900 | 3.8 | 220 | " " " |
| 1000 | 4.4 | 300 | " " " |

FIG. 6

APPARATUS AND METHOD OF STIRRING FLUIDS

This is a continuation, of application Ser. No. 723,883, filed Sept. 16, 1976, now abandoned. su

BACKGROUND OF THE INVENTION

The present invention relates to a novel method of stirring fluid media and to a stirring apparatus. More particularly, the invention relates to the growing of micro-organisms contained in a liquid culture medium within a biological fermentor by mixing air into intimate contact with the micro-organisms.

Biological fermentors with various types of rotor designs are known. Such designs include propellers, turbine wheels, flat blade paddles, armature type agitators, and vibration agitators, all with and without stators. Reference may be had to Ullmannn, Encyclopedia of Technical Chemistry, 1972, vol. 1, page 223.

German Patent No. 1,557,185 discloses a multi-stage rotor having a conduit tube. The fluid to be aerated flows through openings, thereupon flows under high pressure through the conduit tube, and finally flows downwardly between the conduit tube and the walls of the fermentor.

However, all of the known mixing arrangements have the disadvantage that they must be operated at relatively high rotor speeds in order to achieve the desired degree of dispersion of fluid and gas. This high speed requirement results in excessively high wear for the rotor and also in very high input power consumption.

In addition, the known prior-art arrangements have proven particularly unsatisfactory in applications wherein the fluid medium is highly viscous, for example in the vicinity of 50–100 poise. In such cases a uniform homogeneous dispersion is not readily obtainable. Furthermore, the shear forces which are generated at high rotor speeds destroy the myzellium-type growth or upper crust which forms during the manufacture of antibiotics. At lower rotor speeds, the aeration is generally too weak to be effective.

SUMMARY OF THE INVENTION

Accordingly, it is the general object of the present invention to overcome the drawbacks of the prior art.

Another object of the present invention is to achieve a high degree of dispersion efficiency in biological fermentors.

Yet another object of the invention is to minimize the power input but still achieve a high degree of dispersion efficiency in biological fermentors.

Still another object of the invention is to reduce the speed of the rotor as compared with prior-art biological fermentor constructions without sacrificing dispersion efficiency.

In keeping with these objects and others which will become apparent hereinafter, one feature of the invention resides, briefly stated, in a stirring apparatus which comprises a vessel for containing fluid media to be stirred. A rotor is mounted in the vessel for turning movement in a first direction. A baffle element is mounted on the rotor for turning movement with the same and also relative thereto in a second direction opposite to the first direction. A drive means or motor is operative for turning the rotor and baffle element in their respective directions so as to strongly agitate the fluid media.

These features achieve a relatively high degree of dispersion efficiency because of the relatively greater mixing action which is generated by the respective movements of the rotor and baffle element. The speed of the rotor can therefore be reduced, thus minimizing the power input consumption without sacrificing operational efficiency.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 6 is a table listing test results for different modifications of the apparatus.

DESCRIPTION OF THE PREFERRED EMBODIMENTS

Figure 1:
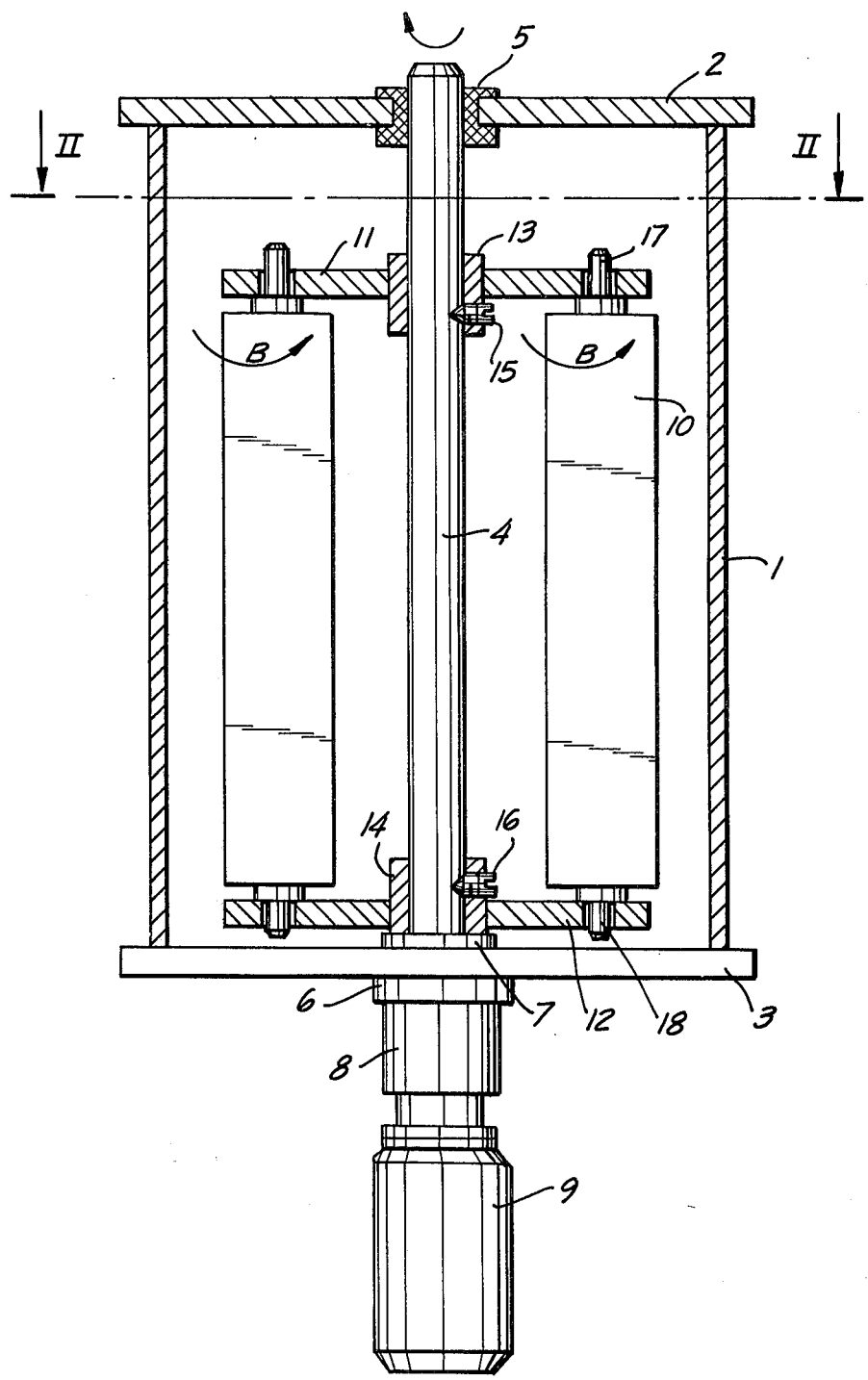
FIG. 1 is a partially sectional view of the apparatus in accordance with the invention.

Describing jointly the novel stirring method and apparatus initially with respect to FIG. 1, it will be seen that reference numeral 1 generally identifies a vessel whose interior is closed by end plates 2 and 3. The vessel 1 may contain any fluid media requiring to be stirred. For example, a preferred embodiment of the invention is directed to the growing of micro-organisms. Thus, the vessel may be a biological reactor or fermentor; and the fluid media are preferably a gas such as air or oxygen and a liquid culture medium which is comprised of nutrients and micro-organisms to be grown.

Figure 2:
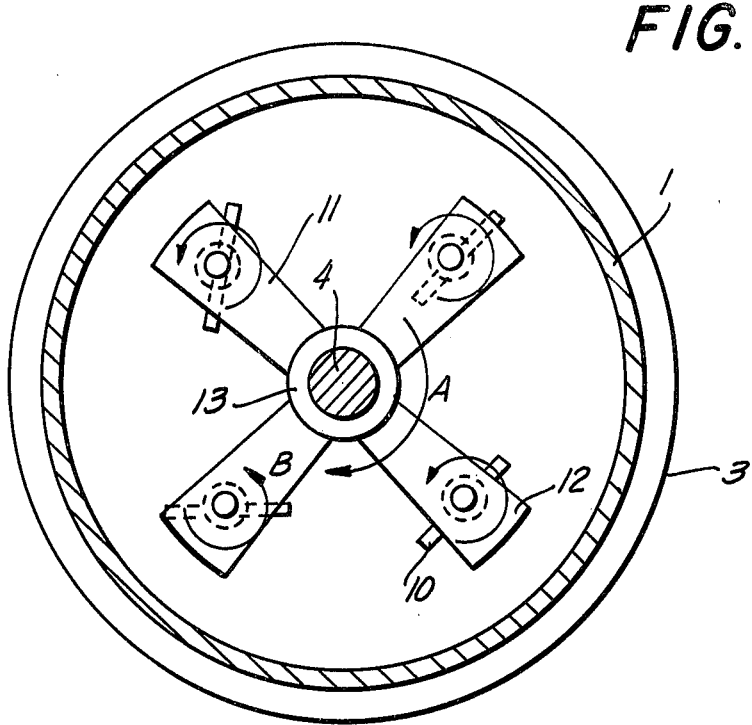
FIG. 2 is a partially sectioned view taken along line II—II of FIG. 1.

An elongated shaft 4 is centrally mounted in vessel 1 for turning movement in a first direction, for example, see clockwise arrow A in FIG. 2. The opposite end regions of shaft 4 are respectively journalled in bearings 5 and 6 which are in turn respectively mounted in end plates 2 and 3. A seal 7 prevents escape of the fluid media from the vessel 1.

Drive means or motor 9 is connected to shaft 4 through transmission 8 and is operative for turning the shaft in the aforementioned first direction.

Support plates 11 and 12 are mounted on shaft 4 in spaced relationship along the shaft. Support plate 11 is fixed by hub 13 and set screw 15; support plate 12 is fixed by hub 14 and set screw 16.

Intermediate the support plates are located baffle elements 10. Journalling portions or pins 17, 18 are located at opposite end regions of each baffle 10 so as to mount the latter on the support for free turning movement in the support plates 11 and 12.

In operation, upon actuation of the drive motor 9, the shaft 4 and the support plates 11 and 12 mounted thereon turn together in a first direction. The baffles 10 also participate in this turning movement but in a direction opposite to the aforementioned first direction, i.e. counterclockwise — see arrow B of FIG. 2 —, by virtue of impingement with the fluid media located within the vessel 1. Thus, the fluid media in the vessel is strongly agitated.

In the preferred embodiment of growing micro-organisms, the gas such as air is introduced into the vessel 1 by a non-illustrated conduit through the end plate 2 to a position in the vicinity of the end plate 3 for mixing with the culture medium contained in the vessel.

Figure 3A:
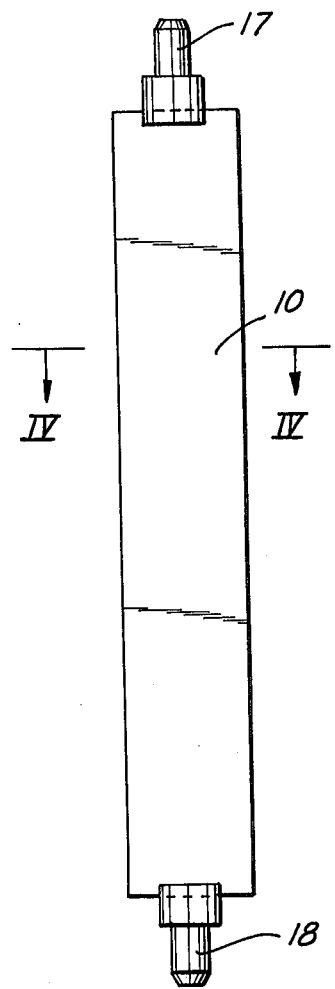
FIG. 3A is a front view of a detail of FIG. 1.
Figure 3B:
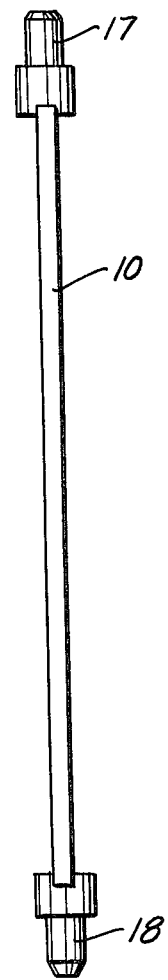
FIG. 3B is a side view of the detail of FIG. 3A.
Figure 4A:
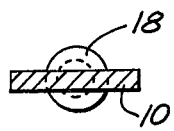
FIG. 4A is a cross-sectional view of the detail of FIG. 1 taken along line IV—IV of FIG. 3A.
Figure 4B:
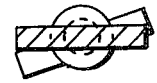
FIG. 4B is a cross-sectional view similar to FIG. 4A of a modified version of the detail of FIG. 1.

FIG. 3A shows a baffle 10 having a planar configuration. FIG. 3B shows the same baffle 10 in side view. FIG. 4A shows the same baffle 10 but in a cross-section view. The baffle 10 need not be planar but can be twisted about its longitudinal axis. In this so-called helix configuration, the baffle 10 has a cross-section configuration as shown in FIG. 4B.

Figure 5:
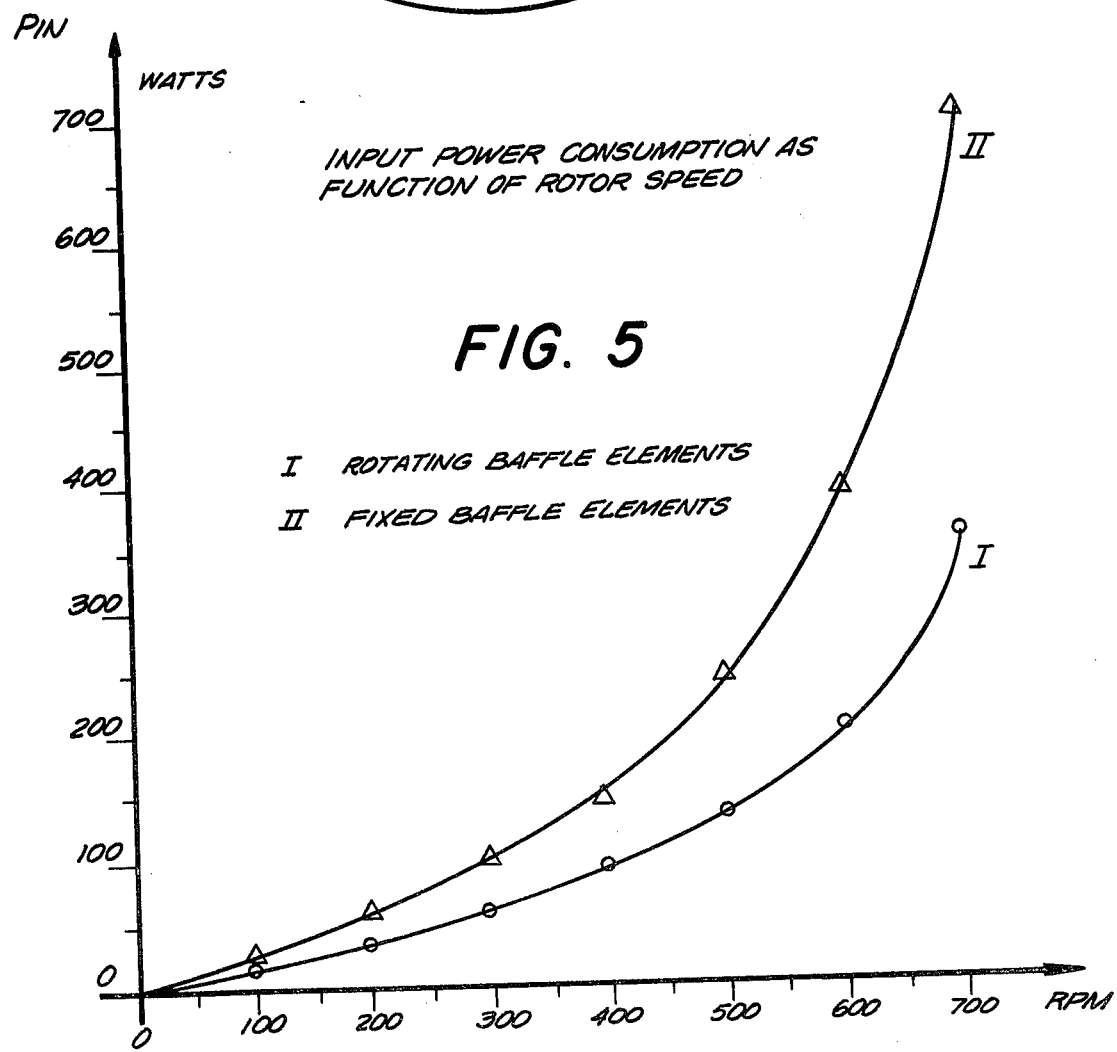
FIG. 5 is a graph comparing different modes of operation for the apparatus in accordance with the invention.

Experiments have been performed and the test results are listed below in order to more particularly set forth the advantageous results obtained with the present invention. Thus FIG. 5 depicts a graph of input power consumption (watts) as a function of the speed of rotation of the shaft (rpm). The curve labelled I identifies the construction of FIG. 1 with freely turnable baffle elements; and the curve labelled II identifies an analogous construction but with fixed baffle elements.

Upon inspection of the graph for example at 400 rpm, the power input consumption is about 220 watts for curve I and about 600 watts for curve II. Hence, there is approximately a 95% lesser requirement for input power when the baffle elements are freely turnable.

FIG. 6 lists additional test results which were taken in a 14 liter vessel containing approximately 11 liters of water. Part (a) is directed to a four baffle construction; part (b) is directed to a two baffle construction. It will be noted that for a given rpm, the observed mixing effect is relatively more turbulent for the four baffle construction as compared with the two baffle construction. The power consumption is, for example, at 200 rpm 50% greater in the four baffle construction as compared with the two baffle construction.

It will be understood that each of the elements described above, or two or more together, may also find a useful application in other types of constructions differing from the types described above.

While the invention has been illustrated and described as embodied in an apparatus and method of stirring, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that from the standpoint of prior art, fairly constitute essential characteristics of the generic of specific aspects of this inventon.

What is claimed as new and desired to be protected by Letters Patent is set forth in the appended claims:

1. A stirring apparatus, particularly for use in mixing a gaseous medium with a liquid medium containing micro-organisms to be grown, comprising an annular vessel for containing the fluid media to be stirred; a rotor mounted in said vessel for turning movement about an axis of rotation; a generally flat baffle element on said rotor and having a longitudinal axis spaced radially from said axis of rotation and two generally flat opposite faces, said baffle element being freely turnably mounted for rotation about its longitudial axis; and drive means for turning said rotor in a first direction about said axis of rotation, and for orbiting said longitudinal axis and thereby said baffle element in said first direction about said axis of rotation along an unobstructed path in which only fluid media to be stirred is present, so that when said baffle element is orbited in said first direction it freely and continuously turns in a second direction opposite to said first direction solely in response to impingement on said baffle element by the fluid media contained in said unobstructed path, and thereby continuously acts by its opposite faces upon the fluid media so as to agitate the latter.

2. An apparatus as defined in claim 1, wherein said vessel is a biological reactor for containing a gas and a culture medium which includes micro-organisms to be grown by aeration with the gas.

3. An apparatus as defined in claim 1, wherein said rotor comprises an elongated shaft connected to said drive means, and a pair of support plates mounted on said shaft in spaced relationship in direction of the elongation of said shaft.

4. An apparatus as defined in claim 3, wherein said baffle element is elongated and has journalling portions at its opposite end regions for mounting said baffle element to said support plates intermediate the latter.

5. An apparatus as defined in claim 1, and further comprising an additional baffle element also mounted on said rotor for turning movement with the same and also relative thereto, said baffle elements being spaced apart of each other and together constituting a pair.

6. An apparatus as defined in claim 5; and further comprising additional pairs of baffle elements.

7. An apparatus as defined in claim 1, wherein said baffle element is constituted of corrosion-resistant steel.

8. An apparatus as defined in claim 1, wherein said baffle element is constituted of synthetic plastic material.

9. An apparatus as defined in claim 1, wherein said baffle element has a twisted configuration.

10. An apparatus as defined in claim 1, wherein said baffle element is planar.

11. A stirring apparatus, particularly for use in mixing a gaseous medium with a liquid medium containing micro-organisms to be grown, comprising an annular vessel for containing the fluid media to be stirred; a rotary shaft mounted in said vessel for turning movement about an axis of rotation; a pair of support plates fixedly mounted on said shaft for turning with the same, said plates being spaced axially apart of each other and having a plurality of radially-extending portions which are formed with journaling passages; a plurality of generally flat baffle elements each having a longitudinal axis and two generally flat opposite faces and being mounted intermediate said support plates at a location in which each longitudinal axis is spaced radially from said axis of rotation; means extending portions of said plates, including a pair of journaling pins at opposite end regions of each baffle element, each journaling pin being receivable in a respective journaling passage for freely turnably mounting the respective baffle element for rotation about its longitudinal axis; and drive means for turning said shaft and said plates in a first direction about said axis of rotation, and for orbiting each longitudinal axis and thereby each baffle element in said first direction about said axis of rotation along an unobstructed path in which only fluid media to be stirred is present, so that when each baffle element is orbited in said first direction it freely and continuously turns in a second direction opposite to said first direction solely in response to impingement on each baffle element by the fluid media contained in said unobstructed path and thereby continuously acts by its opposite faces upon the fluid media so as to agitate the latter.

12. A method of stirring fluid media in a vessel, comprising the steps of mounting a rotor in the vessel for turning movement about an axis of rotation; mounting a generally flat baffle element having a longitudinal axis at a location spaced radially of said axis of rotation and two generally flat opposite faces so that the baffle element is freely turnable on the rotor for rotation about the longitudinal axis; and turning said rotor in a first direction about said axis of rotation, and orbiting said longitudinal axis and thereby the baffle element in said first direction about said axis of rotation along an unobstructed path in which only fluid media to be stirred is present, so that when the baffle element is orbited in said first direction it freely and continuously turns in a second direction opposite to said first direction solely in response to impingement on the baffle element by the fluid media contained in said unobstructed path, and thereby continuously acts by its opposite faces upon the fluid media so as to agitate the latter.

* * * * *